United States Patent
Takahashi et al.

(10) Patent No.: US 12,419,492 B2
(45) Date of Patent: Sep. 23, 2025

(54) INFORMATION PROCESSING DEVICE, DISPLAY METHOD, AND NON-TRANSITORY COMPUTER-READABLE MEDIUM FOR STORING A PROGRAM FOR LESION DETECTION PROCESSING SUPPORTING DECISION MAKING USING MACHINE LEARNING

(71) Applicants: NEC CORPORATION, Tokyo (JP); NATIONAL CANCER CENTER, Tokyo (JP)

(72) Inventors: Ikuma Takahashi, Tokyo (JP); Tatsu Kimura, Tokyo (JP); Kimiyasu Takoh, Tokyo (JP); Kenichi Kamijo, Tokyo (JP); Shota Ohtsuka, Tokyo (JP); Motoyasu Okutsu, Tokyo (JP); Masayoshi Yamada, Tokyo (JP); Ryuji Hamamoto, Tokyo (JP); Yutaka Saito, Tokyo (JP)

(73) Assignees: NEC CORPORATION, Tokyo (JP); NATIONAL CANCER CENTER, Tokyo (JP)

( * ) Notice: Subject to any disclaimer, the term of this patent is extended or adjusted under 35 U.S.C. 154(b) by 348 days.

(21) Appl. No.: 17/915,946

(22) PCT Filed: Mar. 31, 2020

(86) PCT No.: PCT/JP2020/014850
§ 371 (c)(1),
(2) Date: Sep. 29, 2022

(87) PCT Pub. No.: WO2021/199294
PCT Pub. Date: Oct. 7, 2021

(65) Prior Publication Data
US 2023/0337893 A1 Oct. 26, 2023

(51) Int. Cl.
*A61B 1/00* (2006.01)
*A61B 1/04* (2006.01)

(52) U.S. Cl.
CPC .... *A61B 1/000094* (2022.02); *A61B 1/00045* (2013.01); *A61B 1/00055* (2013.01); *A61B 1/04* (2013.01)

(58) Field of Classification Search
None
See application file for complete search history.

(56) References Cited

U.S. PATENT DOCUMENTS

2008/0303898 A1* 12/2008 Nishimura ............. G16H 40/63
348/E7.085
2009/0051695 A1 2/2009 Matsuda
(Continued)

FOREIGN PATENT DOCUMENTS

| | | | |
|---|---|---|---|
| JP | 2006-061469 A | 3/2006 | |
| JP | 2015-173921 A | 10/2015 | |

(Continued)

OTHER PUBLICATIONS

Machine language translation of JP-WO2020039929, Feb. 2020.*
(Continued)

*Primary Examiner* — John P Leubecker
(74) *Attorney, Agent, or Firm* — Sughrue Mion, PLLC

(57) ABSTRACT

Provided are an information processing device, a display method, and a program that allow to easily grasp during examination that a lesion is captured how long before from now which is detected by detection processing for an image captured by an endoscope. An information processing device includes: an image acquisition unit configured to sequentially acquire a current image captured by an endoscope; a lesion detection unit configured to sequentially perform detection processing of a lesion site on the images
(Continued)

sequentially acquired by the image acquisition unit; and a display control unit configured to display, on a display device, a degree of lapse of time up to a current time from a capturing time of the image in which the lesion site is detected by the lesion detection unit.

10 Claims, 9 Drawing Sheets

(56) References Cited

U.S. PATENT DOCUMENTS

| | | | |
|---|---|---|---|
| 2017/0004620 A1* | 1/2017 | Kitamura | G06T 7/0016 |
| 2017/0367559 A1* | 12/2017 | Takahashi | A61B 5/0036 |
| 2019/0114738 A1* | 4/2019 | Sonoda | A61B 1/000094 |
| 2019/0374088 A1* | 12/2019 | Watanabe | A61B 1/0638 |
| 2021/0012495 A1* | 1/2021 | Kamon | G16H 50/20 |
| 2021/0110915 A1* | 4/2021 | Oosake | A61B 1/000094 |
| 2021/0153720 A1* | 5/2021 | Usuda | A61B 1/07 |
| 2021/0153722 A1* | 5/2021 | Karino | A61B 1/00006 |
| 2021/0153821 A1* | 5/2021 | Endo | A61B 1/00045 |
| 2021/0158528 A1* | 5/2021 | Endo | G16H 30/40 |
| 2021/0201486 A1* | 7/2021 | Takenouchi | G06T 7/0012 |
| 2021/0274999 A1* | 9/2021 | Kubota | A61B 1/00045 |

FOREIGN PATENT DOCUMENTS

| | | |
|---|---|---|
| JP | WO2020039929 A1 * | 2/2020 |
| WO | 2017/216922 A1 | 12/2017 |
| WO | 2019/088121 A1 | 5/2019 |
| WO | 2020/021864 A1 | 1/2020 |
| WO | 2020/039685 A1 | 2/2020 |
| WO | 2020/039929 A1 | 2/2020 |
| WO | 2020/054604 A1 | 3/2020 |

OTHER PUBLICATIONS

Extended European Search Report issued Nov. 10, 2023 in Application No. 20929609.4.

International Search Report for PCT/JP2020/014850 dated Jun. 30, 2020 [PCT/ISA/210].

* cited by examiner

INFORMATION PROCESSING DEVICE, DISPLAY METHOD, AND NON-TRANSITORY COMPUTER-READABLE MEDIUM FOR STORING A PROGRAM FOR LESION DETECTION PROCESSING SUPPORTING DECISION MAKING USING MACHINE LEARNING

CROSS REFERENCE TO RELATED APPLICATIONS

This application is a National Stage of International Application No. PCT/JP2020/014850 filed Mar. 31, 2020.

TECHNICAL FIELD

The present disclosure relates to an information processing device, a display method, and a non-transitory computer-readable medium for storing a program.

BACKGROUND ART

A system is known that supports medical treatment using an endoscope. For example, Patent Literature 1 discloses an image display device that displays an image captured by a capsule-type endoscope. The image display device displays a slider indicating a capturing time of an image currently displayed in a main image display area on a time bar indicating an image capturing period of the capsule endoscope.

CITATION LIST

Patent Literature

Patent Literature 1: Japanese Unexamined Patent Application Publication No. 2006-061469

SUMMARY OF INVENTION

Technical Problem

In a case of detection of a lesion by detection processing on an image captured by an endoscope in real time during in-vivo examination using an endoscope, there is a need for a user to confirm a lesion detected by detection processing using an endoscope. When a current position of the endoscope has moved from a position at which the lesion is captured, the user needs to adjust a position of the endoscope in vivo such that the detected lesion is captured again. However, since the user cannot easily grasp what time the lesion detected by the detection processing is captured during the examination, it is difficult to grasp how much the position of the endoscope should be moved. In other words, the user cannot easily grasp, during the examination, that the lesion is captured how long before from now which is detected by the detection processing. On the other hand, since it is not assumed in the technique disclosed in Patent Literature 1 that the user confirms the lesion detected by the detection processing using an endoscope, the user cannot grasp with this technique that the lesion is captured how long before from now which is detected by the detection processing.

The present disclosure has been made in order to solve such problems. Specifically, an object of the present disclosure is to provide an information processing device, a display method, and a program that allow to easily grasp during examination that a lesion is captured how long before from now which is detected by detection processing for an image captured by an endoscope.

Solution to Problem

An information processing device according to a first aspect of the present disclosure includes:
an image acquisition unit configured to sequentially acquire a current image captured by an endoscope;
a lesion detection unit configured to sequentially perform detection processing of a lesion site on the images sequentially acquired by the image acquisition unit; and
a display control unit configured to display, on a display device, a degree of lapse of time up to a current time from a capturing time of the image in which the lesion site is detected by the lesion detection unit.

A display method according to a second aspect of the present disclosure includes:
sequentially acquiring a current image captured by an endoscope;
sequentially performing detection processing of a lesion site on the images sequentially acquired; and
displaying, on a display device, a degree of lapse of time up to a current time from a capturing time of the image in which the lesion site is detected.

A program according to a third aspect of the present disclosure causes a computer to execute:
an image acquisition step of sequentially acquiring a current image captured by an endoscope;
a lesion detection step of sequentially performing detection processing of a lesion site on the images sequentially acquired; and
a display control step of displaying, on a display device, a degree of lapse of time up to a current time from a capturing time of the image in which the lesion site is detected.

Advantageous Effects of Invention

According to the present disclosure, it is possible to provide an information processing device, a display method, and a program that allow to easily grasp during examination that a lesion is captured how long before from now which is detected by detection processing for an image captured by an endoscope.

EXAMPLE EMBODIMENT

Figure 1:
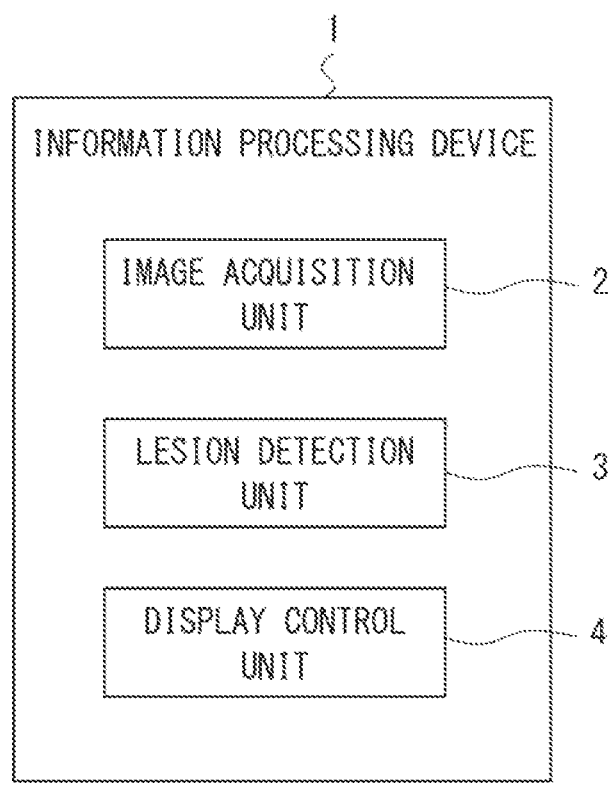
FIG. 1 is a block diagram showing an example of a configuration of an information processing device according to a first example embodiment.

For clarifying the explanation, the following descriptions and the drawings are omitted and simplified as appropriate. In each drawing, the same or corresponding components are designated by the same reference numerals, and duplicate descriptions are omitted as necessary for the sake of clarity of explanation. In addition, the features of each example embodiment can be combined as long as there is no technical contradiction.

<First Example Embodiment>

FIG. 1 is a block diagram showing an example of a configuration of an information processing device 1 according to a first example embodiment. The information processing device 1 is a device that supports an examination by a user (for example, a doctor) using an endoscope, and performs detection processing of a lesion using an image captured by the endoscope and display processing based on detection results. As shown in FIG. 1, the information processing device 1 includes an image acquisition unit 2, a lesion detection unit 3, and a display control unit 4.

The image acquisition unit 2 sequentially acquires current images captured by the endoscope. Specifically, the image acquisition unit 2 sequentially acquires each frame image constituting a moving image captured by the endoscope.

The lesion detection unit 3 sequentially performs detection processing of a lesion site on the images sequentially acquired by the image acquisition unit 2.

The lesion detection unit 3 performs any image recognition processing to detect a lesion site depicted in an image. Here, the lesion refers to an abnormality in a biological tissue caused by a disease or the like, the abnormality including, for example, a polyp or a tumor, but being not limited thereto.

The display control unit 4 controls a display of information on a display device. Specifically, the display control unit 4 causes a display device to display a degree of lapse of time up to now from the capturing time of the image where the lesion site is detected by the lesion detection unit 3. The degree of lapse can be said to be an index indicating that the lesion has been detected in the image captured how long before from now. Any display aspect can be adopted as a display aspect of the degree of lapse. The display control unit 4 may graphically display the degree of lapse, or may display a numerical value indicating the lapse of time up to the current time as will be described in example embodiments described below.

According to the present example embodiment, the display control unit 4 controls the display device to display the degree of lapse of time up to now from the capturing time of the image where the lesion site is detected by the lesion detection unit 3. For this reason, the user can easily grasp what time the lesion detected by the detection processing is captured during the examination. In other words, according to the information processing device 1 or the display method realized by the above-described processing, it is possible to easily grasp, during the examination, that the lesion is captured how long before from now which is detected by the detection processing on the image captured by the endoscope.

The information processing device 1 includes a processor and a memory as components which are not shown. The processor reads a computer program, in which the above-described processing of the information processing device 1 is implemented, from the memory, and executes the computer program. Thus, the processor realizes functions of the image acquisition unit 2, the lesion detection unit 3, and the display control unit 4.

Alternatively, each of the image acquisition unit 2, the lesion detection unit 3, and the display control unit 4 may be realized by dedicated hardware. Further, a part or all of components of each device may be realized by a general-purpose or dedicated circuitry, a processor, or a combination thereof. The components may be configured by a single chip, or may be configured by a plurality of chips connected to each other via a bus. A part or all of components of each device may be realized by a combination of the circuitry and the program described above. In addition, as a processor, a CPU (Central Processing Unit), a GPU (Graphics Processing Unit) or the like can be used.

Further, when a part or all of the components of the information processing device 1 are realized by a plurality of information processing devices and circuits, the plurality of information processing devices and the circuits may be arranged in a centralized manner, or may be arranged in a distributed manner. For example, the information processing devices and the circuits may be realized as a form of being connected to each other via a communication network such as a client-and-server system or a cloud computing system. Further, the function of the information processing device 1 may be provided in SaaS (Software as a Service) format.

Example embodiments will be described below in which the first example embodiment is made more specific.

<Second Example Embodiment>

Figure 2:
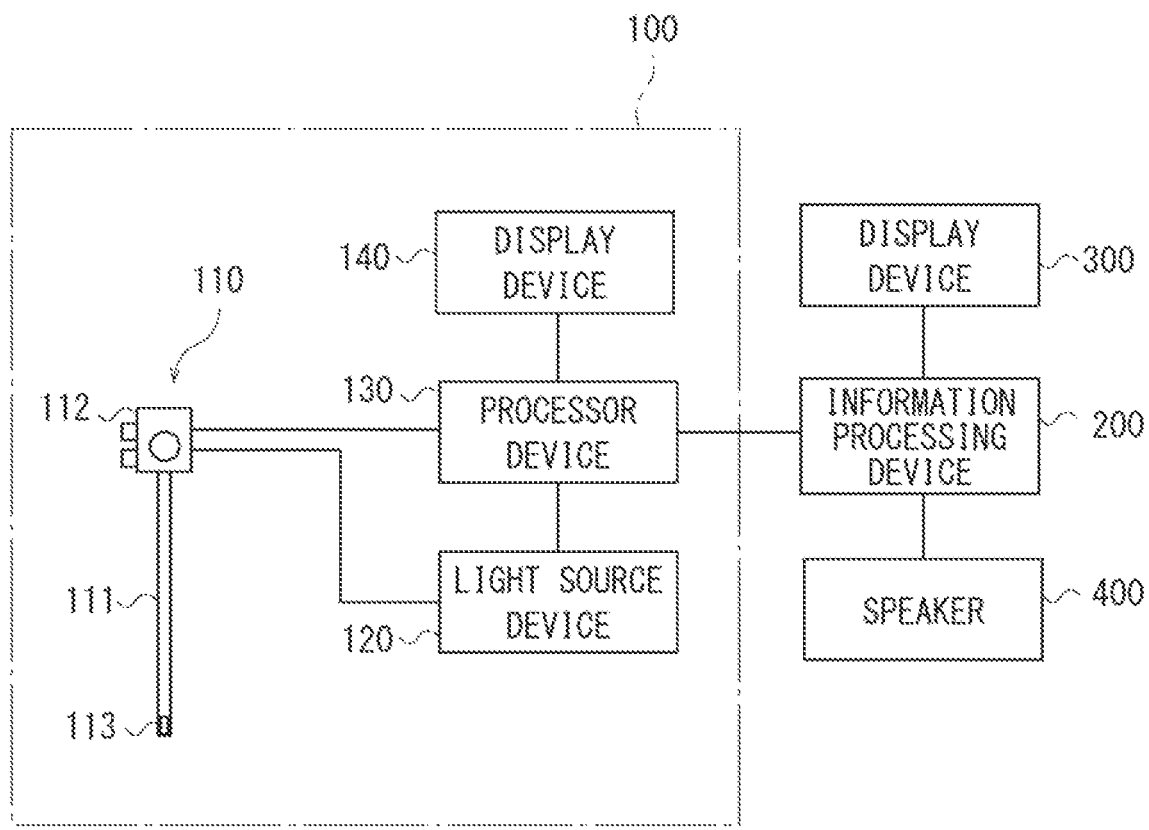
FIG. 2 is a block diagram showing a configuration of an examination support system according to a second example embodiment.

FIG. 2 is a block diagram showing a configuration of an examination support system 10 according to a second example embodiment. The examination support system 10 includes an endoscope system 100, an information processing device 200, a display device 300, and a speaker 400. The endoscope system 100 is used to examine body cavities of a subject to be examined. For example, the endoscope system 100 is used to examine a large intestine, but may be used to examine other digestive tracts.

The endoscope system 100 includes an endoscope 110, a light source device 120, a processor device 130, and a display device 140. The endoscope 110 is optically connected to the light source device 120, and further electrically connected to the processor device 130.

The endoscope 110 includes an insertion portion 111 (an insertion unit 111) to be inserted into the body of a person who is a subject to be examined and an operation portion 112 (an operation unit 112) configured to operate a direction of a distal end of the insertion portion 111. An image capturing portion 113 (an image capturing unit 113) is provided at the endoscope 110 to capture an in-vivo image of the body. The image capturing portion 113 includes, for example, various lenses, an image capturing sensor, and a signal processing circuit. As the image capturing sensor, for example, a sensor such as a CCD (Charge Coupled Device) or a CMOS (Complementary Metal-Oxide Semiconductor) is used. The various lenses and the image capturing sensor are disposed at the distal end of the insertion portion 111, for example, and the other signal processing circuits are disposed at the operation portion 112, for example. The image capturing portion 113 outputs an image signal of the captured image to the processor device 130 under the control of the processor device 130.

A light guide is provided inside the insertion portion 111 to propagate illumination light from the light source device 120 to the distal end of the insertion portion 111, and the inside of the body can be illuminated by the illumination light. Further, the insertion portion 111 is provided with a treatment-instrument insertion passage through which a treatment instrument such as electrocautery is guided from the operation portion 112 to the distal end of the insertion portion 111. Therefore, the user (doctor) can excise the lesion site with the treatment instrument while looking at the image captured by the endoscope 110. In addition, the insertion portion 111 is provided with a nozzle for ejecting air or water from the distal end of the insertion portion 111.

The light source device 120 is a device that supplies the illumination light to the above-described light guide provided in the endoscope 110 under the control of the processor device 130. The illumination light output from the light source device 120 is emitted from the distal end of the endoscope 110 by passing through the light guide. Thus, an in-vivo observation site is irradiated with the illumination light.

Figure 3:
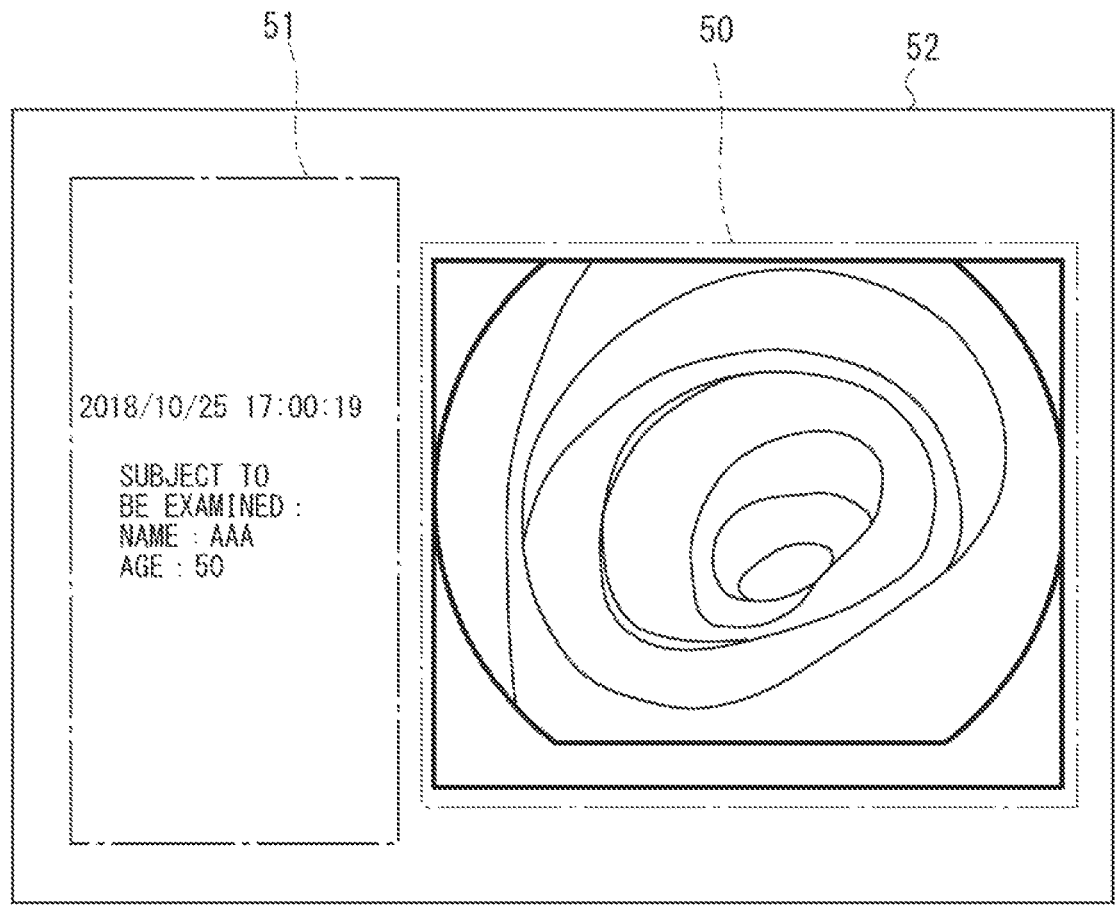
FIG. 3 is a schematic diagram showing an example of a display screen generated by a processor device.

The processor device 130 is electrically connected to the endoscope 110, the light source device 120, the display device 140, and the information processing device 200. The processor device 130 comprehensively controls an operation of the endoscope system 100. Particularly, the processor device 130 performs predetermined image processing on the image signal received from the endoscope 110, and generates a captured image to be displayed on the display device 140. Further, as shown in FIG. 3, the processor device 130 generates a display image 52 in which a captured image is arranged in a captured image area 50 and characters or images of various reference information such as information on the subject to be examined are arranged in a non-captured image area 51. The display image 52 is an image displayed on the entire screen of the display device 140. The processor device 130 controls the display device 140 to display the display image 52. In addition, the processor device 130 outputs the display image 52 to the information processing device 200. The processor device 130 may output the captured image to the information processing device 200. In this way, the processor device 130 outputs the display image 52 or the captured image to the information processing device 200, and thus sequentially outputs the current image captured by the endoscope 110 to the information processing device 200. In other words, the processor device 130 outputs the moving image captured by the endoscope 110, that is, a series of images of the body cavity captured continuously in time to the information processing device 200 in real time.

The processor device 130 includes, for example, a memory and a processor such as a CPU and a GPU, and the processor reads software (computer program) including one or more commands from the memory and executes the software to realize the processing of the processor device 130.

The display device 140 displays the display image 52 generated by the processor device 130. Specifically, the display device 140 is a flat panel display such as a liquid crystal display, a plasma display, or an organic EL (Electro-Luminescence) display.

Next, the information processing device 200, the display device 300, and the speaker 400 will be described.

The display device 300 is electrically connected to the information processing device 200, and is a device that displays an image under the control of the information processing device 200. Specifically, the display device 300 is a flat panel display such as a liquid crystal display, a plasma display, or an organic EL display. The speaker 400 is electrically connected to the information processing device 200, and outputs sound under the control of the information processing device 200.

The information processing device 200 corresponds to the information processing device 1 shown in FIG. 1, and is a device that supports the examination by the user (for example, a doctor). Details of the information processing device 200 will be described below.

Figure 4:
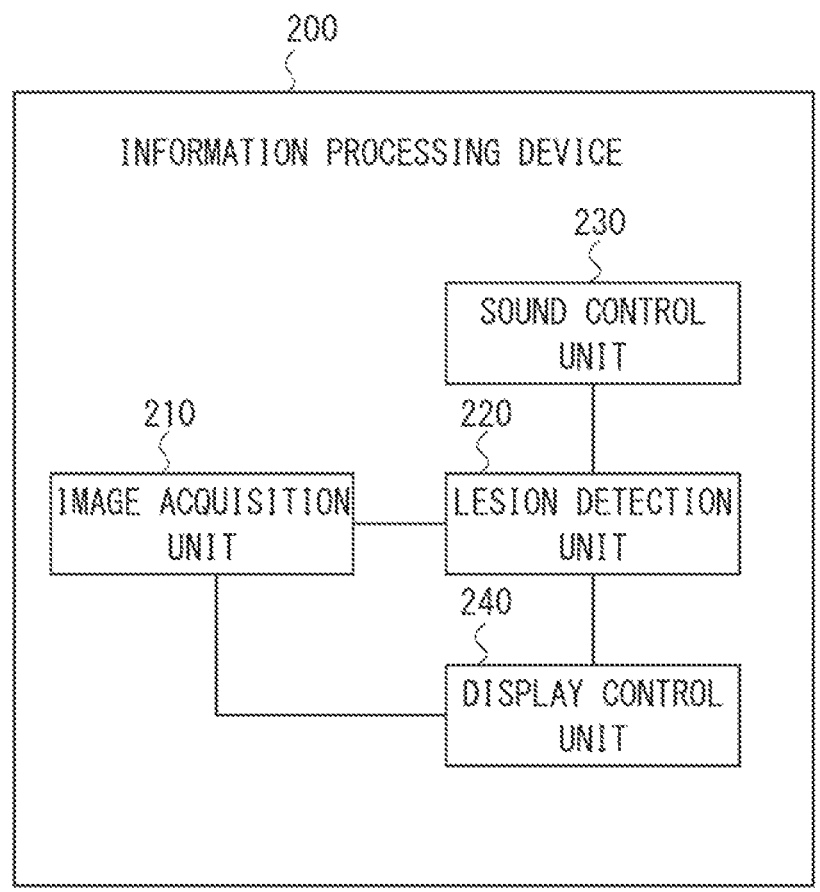
FIG. 4 is a block diagram showing an example of a functional configuration of an information processing device according to the second example embodiment.

FIG. 4 is a block diagram showing an example of a functional configuration of the information processing device 200. As shown in FIG. 4, the information processing device 200 includes an image acquisition unit 210, a lesion detection unit 220, a sound control unit 230, and a display control unit 240.

The image acquisition unit 210 corresponds to the image acquisition unit 2 shown in FIG. 1, and sequentially acquires the current images captured by the endoscope 110. More specifically, the image acquisition unit 210 sequentially acquires in real time a series of images of the body cavity captured continuously in time. In other words, the image acquisition unit 210 sequentially acquires each frame image (still image) constituting the captured moving image in real time. When the display image 52 is output from the processor device 130, the image acquisition unit 210 performs processing of cutting out the captured image arranged in the captured image area 50 from the display image 52.

The lesion detection unit 220 corresponds to the lesion detection unit 3 shown in FIG. 1, and sequentially performs detection processing of a lesion site on the images sequentially acquired by the image acquisition unit 210. In other words, the lesion detection unit 220 sequentially performs detection processing of a lesion site on each frame image constituting the captured moving image. The lesion detection unit 220 performs the detection processing of the lesion site in real time. For example, the lesion detection unit 220 preferably performs the detection processing at a processing speed faster than a frame rate of the captured moving image. The lesion detection unit 220 detects the lesion site from the image by performing known image recognition processing. In such detection processing, a position of the lesion site in the image is also detected. For example, the lesion detection unit 220 performs the detection processing of the lesion site by inputting the image, which is acquired by the image acquisition unit 210, to a model learned in advance by a machine learning algorithm. Such a model is, for example, a model learned by deep learning such as CNN (Convolution Neural Network), but may be a model learned by using another machine learning algorithm. For example, based on whether an index value (accuracy) indicating the probability that the lesion site is depicted in an image output from the model described above exceeds a predetermined threshold value, the lesion detection unit 220 determines whether the lesion site is depicted in the image. Hereinafter, the image including the lesion site, that is, the image in which the lesion site is detected is also referred to as a lesion image.

When detecting the lesion site, the lesion detection unit 220 stores the lesion image, position information in the image of the detected lesion site, the index value described above, and information indicating the capturing time of the lesion image (hereinafter, referred to as capturing time information) in a storage device such as a memory 291, which will be described below. Here, the capturing time information may be any information that can specify a time when the capturing is performed how long before from the current time. For example, the capturing time information is a system time at the time of the capturing. As described above, the captured image is acquired by the image acquisition unit 210 in real time, and the lesion detection processing is performed in real time. Therefore, the lesion detection unit 220 may use the time when the information processing device 200 acquires the image, as capturing time information of the image, or may use the time when the lesion detection unit 220 performs the lesion detection processing, as capturing time information of the image. In addition, the capturing time information may be incidental information attached to the image data by the processor device 130. As described above, the capturing time information may be any information that can specify the time when the capturing is performed how long before from the current time, and thus the frame number of the moving image may be used instead of the system time. This is because it is possible to specify that the captured image, in which the lesion is detected, is captured how long before from now, based on the frame number of the latest captured image (currently captured image), the frame number of the past captured image in which the lesion is detected, and the frame rate of the moving image.

The sound control unit 230 controls the output of the speaker 400. When the lesion detection unit 220 detects the lesion site in the detection processing in real time, the sound control unit 230 outputs a sound from the speaker 400 to notify the detection. Thus, it is possible to notify the user of the detection of the lesion site. For example, the user who hears such a sound can adjust the capturing position of the endoscope 110 to search for the lesion site detected by the information processing device 200. As will be described below, the display device 300 displays an index indicating that the lesion site has been detected in the image captured how long before from now. For this reason, the user can easily grasp how much the position of the endoscope 110 should be set back from the current position by confirming the index. Therefore, the user can easily adjust the position of the endoscope 110 in the living body by display control to be described below such that the detected lesion is captured again.

The display control unit 240 controls the display of the display device 300. The display control unit 240 corresponds to the display control unit 4 shown in FIG. 1. Therefore, in particular, the display control unit 240 causes the display device 300 to display a degree of lapse of time up to now from the capturing time of the lesion image that is found by the processing of the lesion detection unit 220. The display control unit 240 refers to the capturing time information of the lesion image and calculates a lapse of time from the time when the lesion image is captured, thereby specifying the degree of lapse of the lesion image.

Figure 5:
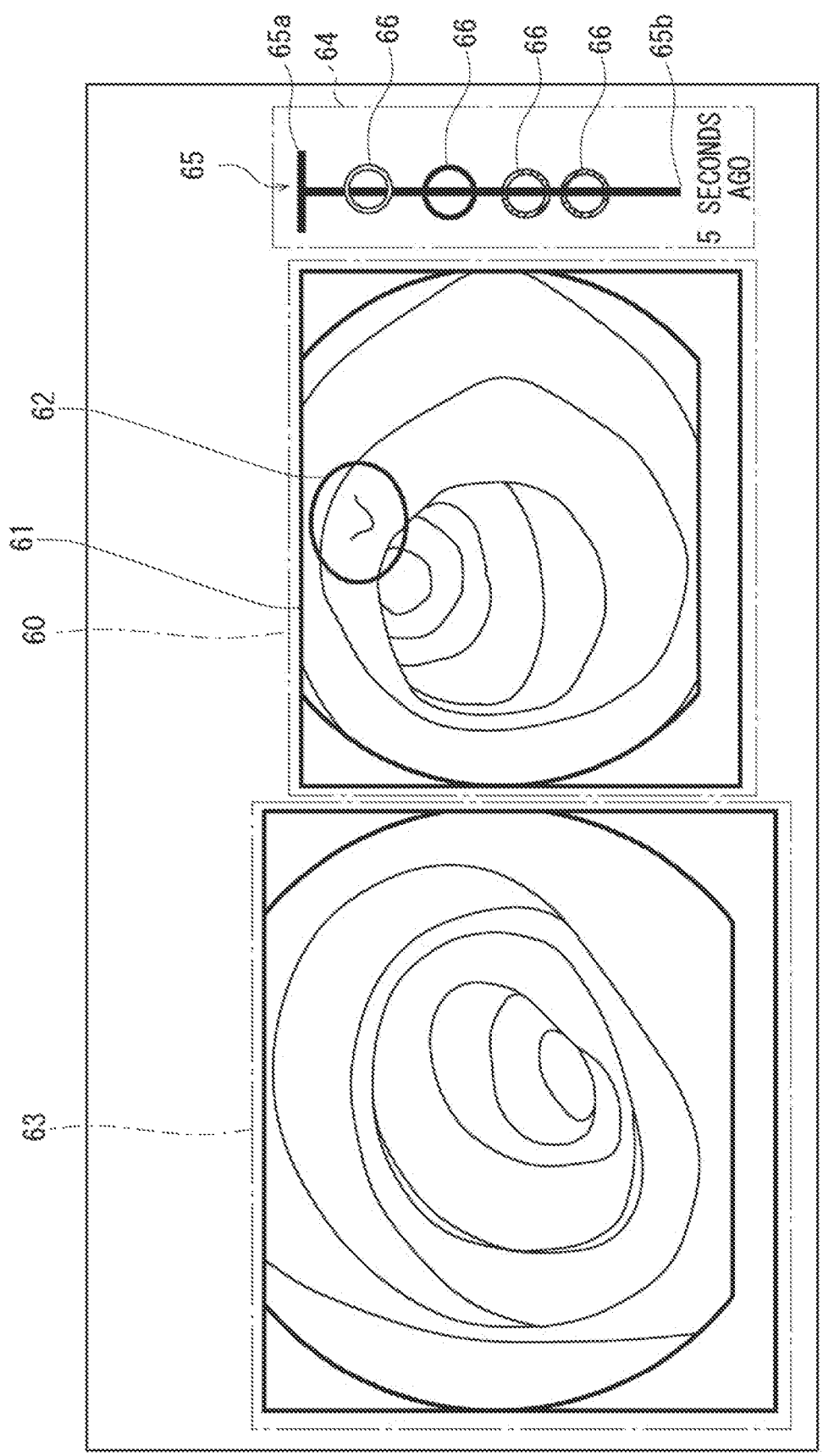
FIG. 5 is a schematic diagram showing a display example based on control of a display control unit.

FIG. 5 is a schematic diagram showing a display example of the display device 300 based on the control of the display control unit 240. The display control of the display control unit 240 of the present example embodiment will be described with reference to FIG. 5.

The display control unit 240 displays, in a lesion image area 60 on the screen of the display device 300, an image 61 in which a lesion site is detected by the lesion detection unit 220. In the example shown in FIG. 5, the latest detected lesion image is displayed in the lesion image area 60. Thus, the user can confirm the image in which the lesion is detected by the information processing device 200.

Further, the display control unit 240 further displays the position of the lesion site detected by the lesion detection unit 220 in the image 61. In the example shown in FIG. 5, specifically, the display control unit 240 displays a frame 62 surrounding the lesion site on the image 61. The display control unit 240 determines a display position of the frame 62 based on position information of the lesion site output by the lesion detection unit 220. Since the display indicating the position of the lesion site is performed, the user can easily confirm a site where the information processing device 200 detects the lesion.

Further, the display control unit 240 displays, in a captured image area 63 on the screen of the display device 300, the current image captured by the endoscope 110 and sequentially acquired from the processor device 130 by the image acquisition unit 210. Thus, the lesion image in the lesion image area 60 and the current image captured by the endoscope 110 are displayed side by side on the display device 300. Since both the images are displayed at the same time in this way, when the user wants to confirm the lesion site detected by the information processing device 200 with the endoscope 110, the user can compare the lesion site detected by the information processing device 200 with the current image captured by the endoscope 110. Therefore, the user more conveniently confirms the lesion site detected by the information processing device 200 with the endoscope 110.

In addition, the display control unit 240 displays, in a lapse-of-time area 64 on the screen of the display device 300, the degree of lapse of time for the lesion image specified during the examination. In the present example embodiment, the display control unit 240 displays a mark 66 indicating the capturing time of the image, in which the lesion site is detected by the lesion detection unit 220, on a time axis 65 with a current time as a starting point, and thus displays the degree of lapse. In the example shown in FIG. 5, the mark 66 is a circle mark, but a mark of another design may be used.

One end 65a of the time axis 65 represents a current time, and the other end 65b of the time axis 65 represents a time that goes back by a predetermined period from the current time. In the example shown in FIG. 5, the period from the current time to 5 seconds before is represented by the time axis 65, but the predetermined period is not limited to 5 seconds and any time can be set. As described above, each of the marks 66 represents the capturing time of the lesion image. As the time advances, the capturing time of the lesion image transitions to a time in the distant past. Therefore, the display control unit 240 moves the display position of the mark 66 on the time axis 65 with the transition of time. In the example shown in FIG. 5, the display control unit 240 displays the mark 66 so as to flow downward along the time axis 65 as the time advances. As described above, in the present example embodiment, since the mark 66 indicating the capturing time of the lesion image is displayed on the time axis 65, the degree of lapse of time for the capturing time is graphically displayed. For this reason, the user can visually grasp with ease the degree of lapse for the capturing time of the lesion image.

As shown in FIG. 5, the display control unit 240 displays the degree of lapse for the image, which is captured up to the time of a predetermined period (5 seconds as an example in FIG. 5) ago from the current time, among the images sequentially acquired by the image acquisition unit 210. In other words, the display control unit 240 does not display the degree of lapse for all the lesions detected during the examination, but displays the degree of lapse for the lesions detected in the latest period. When the degree of lapse is displayed for the entire period from the start of the examination to the current time, a large amount of information will be displayed on a limited screen size, and visibility of the information will be reduced. On the other hand, when the degree of lapse is displayed only for the lesions detected in the latest period, the degree of lapse for the lesion detected in the latest period can be displayed in an easy-to-understand manner. The need for the user to confirm the lesion detected by the information processing device 200 using the endoscope 110, that is, the need to adjust the position of the endoscope 110 for re-capturing of the lesion often occurs immediately after the lesion is detected. For this reason, when the degree of lapse is displayed only in the latest period, the convenience of the user can be improved. The display control unit 240 may display the degree of lapse for the entire period from the start of the examination to the current time.

The display control unit 240 may display the mark 66 depending on the accuracy of the detection in the detection processing. Specifically, the display control unit 240 may display the mark 66 depending on an index value of the image determined to be the lesion image by the lesion detection unit 220. In other words, the display control unit 240 may display a mark 66 having a different design depending on the index value. As described above, the index value represents the probability that the lesion site is depicted in the image, and is output by the lesion detection unit 220. For example, the display control unit 240 may display marks 66 having different colors depending on the index value.

A shape or a pattern may be changed instead of the color. Thereby, the user can easily grasp the reliability of the result detected by the information processing device 200.

The display control unit 240 may change the display aspect of the mark 66 depending on other factors without being limited to the accuracy of detection. For example, the display control unit 240 may display a mark 66 depending on the size of the lesion site detected by the lesion detection unit 220 or a diagnosis result (whether it is benign, or the degree of malignancy).

Further, when a plurality of lesion sites are detected by the lesion detection unit 220 on the same image, the display control unit 240 may display a mark 66 depending on the number of detected lesion sites. In other words, the display control unit 240 may display marks 66 having different designs depending on the number of detected lesion sites. Further, the display control unit 240 may display a value indicating the number of detected lesion sites in the vicinity of the mark 66. Thereby, the user can easily grasp the number of detected lesion sites.

Figure 6:
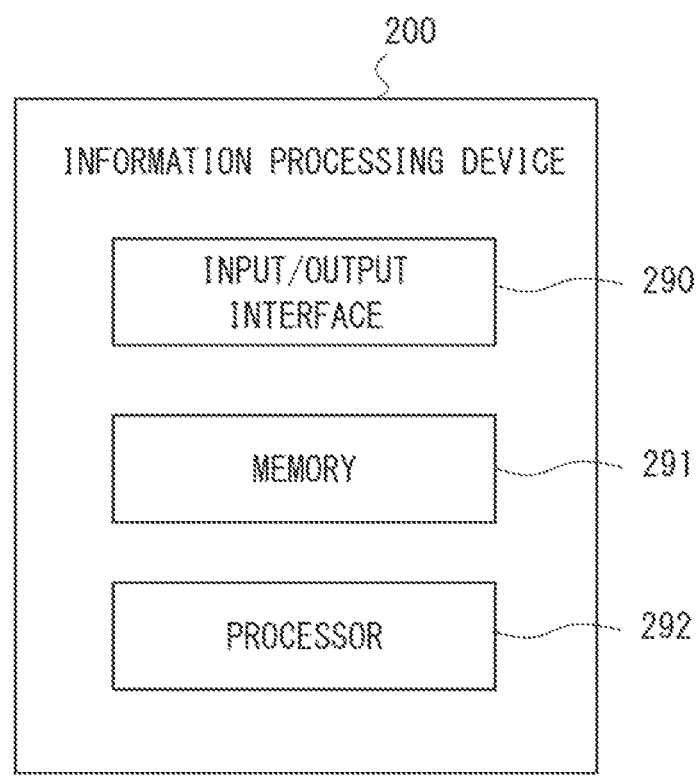
FIG. 6 is a schematic diagram showing an example of a hardware configuration of the information processing device according to the second example embodiment.

An example of a hardware configuration of the information processing device 200 will be described below. FIG. 6 is a schematic diagram showing an example of a hardware configuration of the information processing device 200. As shown in FIG. 6, the information processing device 200 includes an input/output interface 290, a memory 291, and a processor 292.

The input/output interface 290 is an input/output circuit configured to communicate with any other devices, for example, the processor device 130, the display device 300, and the speaker 400.

The memory 291 is configured by a combination of a volatile memory and a non-volatile memory, for example. The memory 291 is used to store software (computer program) and data used for various processing of the information processing device 200, the software including one or more commands executed by the processor 292.

The processor 292 reads and executes the software (computer program) from the memory 291 to perform the processing of each component shown in FIG. 4. Specifically, the processor 292 performs the processing of the image acquisition unit 210, the lesion detection unit 220, the sound control unit 230, and the display control unit 240.

The processor 292 may be, for example, a CPU or a GPU. The processor 292 may include a plurality of processors.

As described above, the information processing device 200 has a function as a computer.

The above-described programs may be stored and supplied to a computer using various types of non-transitory computer readable media. The non-transitory computer readable media include various types of tangible storage media. Examples of the non-transitory computer readable media include a magnetic recording medium (for example, a flexible disk, a magnetic tape, and a hard disk drive), a magneto-optic recording medium (for example, a magneto-optic disk), a CD-ROM (Read Only Memory), a CD-R, a CD-R/W, and a semiconductor memory (for example, a mask ROM, a PROM (Programmable ROM), an EPROM (Erasable PROM), a flash ROM, and a RAM (Random Access Memory)). These programs may be supplied to computers using various types of transitory computer readable media. Examples of the transitory computer readable media include an electrical signal, an optical signal, and an electromagnetic wave. The transitory computer readable media can supply programs to a computer through a wired communication line, for example, electric wires and optical fibers, or a wireless communication line.

Figure 7:
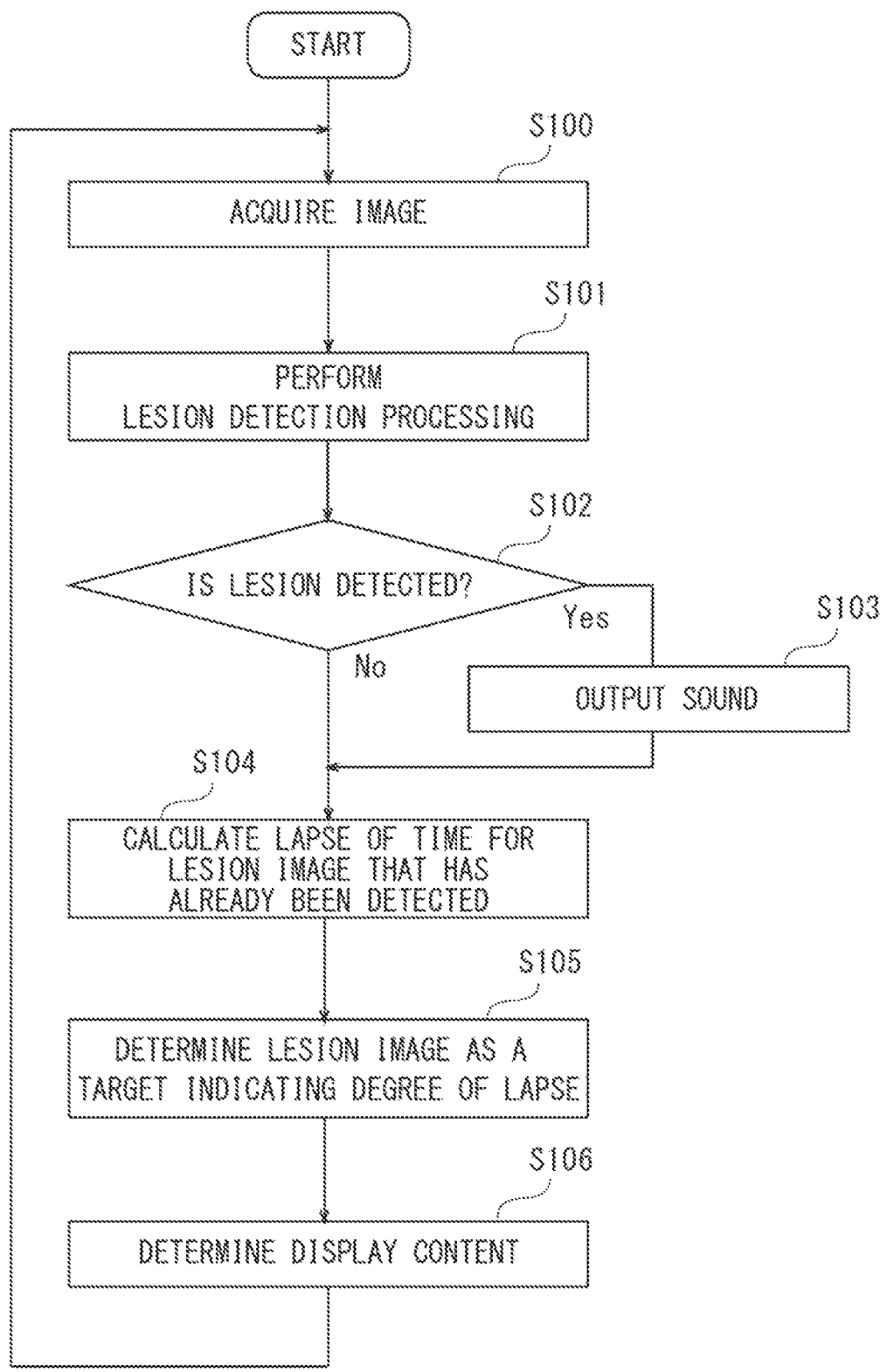
FIG. 7 is a flowchart showing an example of an operation of the information processing device during examination by an endoscope.

An operation example of the information processing device 200 will be described below. FIG. 7 is a flowchart showing an example of the operation of the information processing device 200 during the examination with the endoscope 110. The operation example will be described below with reference to the flowchart of FIG. 7.

In step S100, the image acquisition unit 210 acquires the current image output from the processor device 130 and captured by the endoscope 110.

Next, in step S101, the lesion detection unit 220 performs lesion detection processing on the image acquired in step S100. When the lesion is detected from the image (Yes in step S102), the process proceeds to step S103. When the lesion is not detected from the image (No in step S102), the process proceeds to step S104.

In step S103, the sound control unit 230 outputs the sound from the speaker 400 to notify that the lesion is detected. After step S103, the process proceeds to step S104.

In step S104, the display control unit 240 calculates the lapse of time after the capturing of the lesion images that have already been detected between the start of the examination and the current time. Thus, the display control unit 240 specifies the degree of lapse of time for the detected lesion image.

Next, in step S105, the display control unit 240 determines the lesion image, as a target to be displayed with the degree of lapse, from the lesion images that have already been detected between the start of the examination and the current time. Specifically, the display control unit 240 uses, as a display target of the degree of lapse, the lesion image for which the lapse of time is within the range of the time axis 65. In other words, the display control unit 240 sets, as a display target of the degree of lapse, the lesion image which is captured up to the time of the predetermined period (5 seconds as an example in FIG. 5) ago from the current time.

Next, in step S106, the display control unit 240 determines display contents of the display device 300. Specifically, the display control unit 240 displays the latest detected lesion image and displays the frame 62 surrounding the lesion site on the lesion image, in the lesion image area 60. Further, the display control unit 240 displays the current image captured by the endoscope 110 in the captured image area 63. Then, the display control unit 240 displays, in the lapse-of-time area 64, the degree of lapse for the lesion image determined as the display target of the degree of lapse in step S105. After step S106, the process returns to step S100, and the above-described process is performed on the next image.

The second example embodiment has been described above. According to the present example embodiment, the display control unit 240 displays the degree of lapse of time up to the current time from the capturing time of the image in which the lesion site is detected by the lesion detection unit 220, using the time axis 65 and the mark 66. For this reason, since the degree of lapse is displayed graphically, the user can visually grasp with ease the time when the lesion detected by the detection processing of the information processing device 200 has been captured during the examination. In other words, the user can visually grasp with ease during the examination that the lesion is captured how long before from now which is detected by the detection processing of the information processing device 200. For this reason, the user can easily guess how much the endoscope 110 should be moved in order to capture the lesion again with the endoscope 110.

<Third Example Embodiment>

Figure 8:
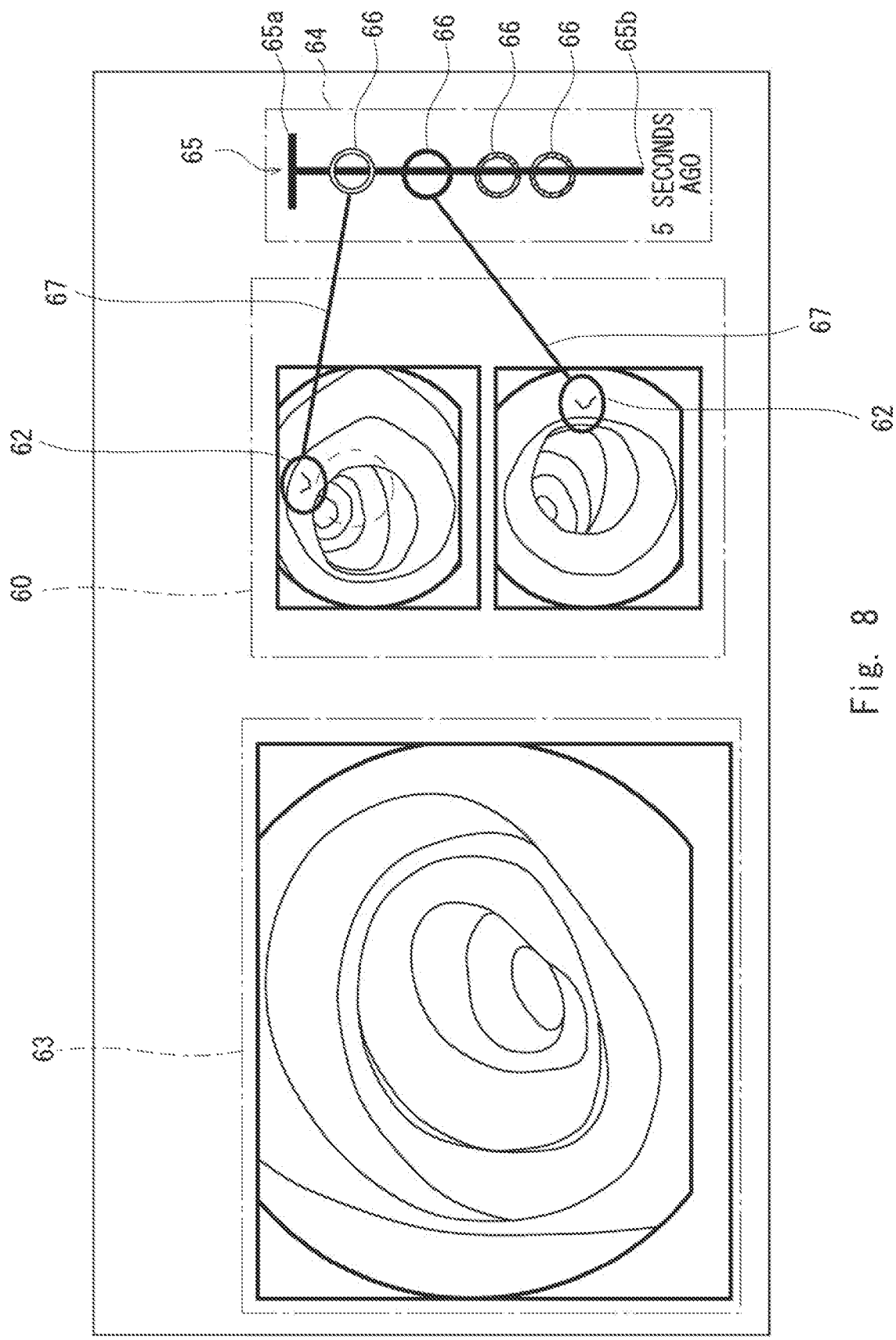
FIG. 8 is a schematic diagram showing a display example based on control of a display control unit.

A third example embodiment will be described below. The display control unit 240 displays one lesion image in the lesion image area 60 on the screen of the display device 300 in the second example embodiment, but a plurality of lesion images may be displayed. Hereinafter, differences from the second example embodiment will be described, and duplicated descriptions of the configuration and process will not be made. In the present example embodiment, when the lesion detection unit 220 detects a plurality of lesion images during the examination, the display control unit 240 displays the plurality of lesion images in the lesion image area 60 as shown in FIG. 8. The display control unit 240 may set an upper limit on the number of lesion images to be displayed. For example, the display control unit 240 may display a maximum of N (where N is a positive integer) lesion images detected most recently. When the value of N is 1, one lesion image is displayed as in the second example embodiment.

By the way, when a plurality of lesion images are displayed, it is difficult to understand a correspondence relation between the mark 66 indicating the degree of lapse and the lesion site. For this reason, as shown in FIG. 8, the display control unit 240 may display a line 67 that associates the position of the lesion site detected in the image by the lesion detection unit 220 with the mark 66. Thereby, the degree of lapse for each lesion image can be easily determined. The line 67, which associates the position of the lesion site in the image with the mark 66, may be displayed regardless of the number of lesion images to be displayed. In other words, the line 67 may be displayed even when only one lesion image is displayed. Further, when a plurality of lesion sites are detected in one lesion image, the line 67 may be displayed for each of the lesion sites.

<Fourth Example Embodiment>

A fourth example embodiment will be described below. In the above-described example embodiments, when the lesion detection unit 220 detects the same lesion site in a plurality of images, the degree of lapse can be displayed for each of the images. Therefore, the visibility of the degree of lapse may decrease. Therefore, in the present example embodiment, the degree of lapse for the same lesion site is not displayed for each image. In the fourth example embodiment, the information processing device 200 is replaced with an information processing device 500.

Figure 9:
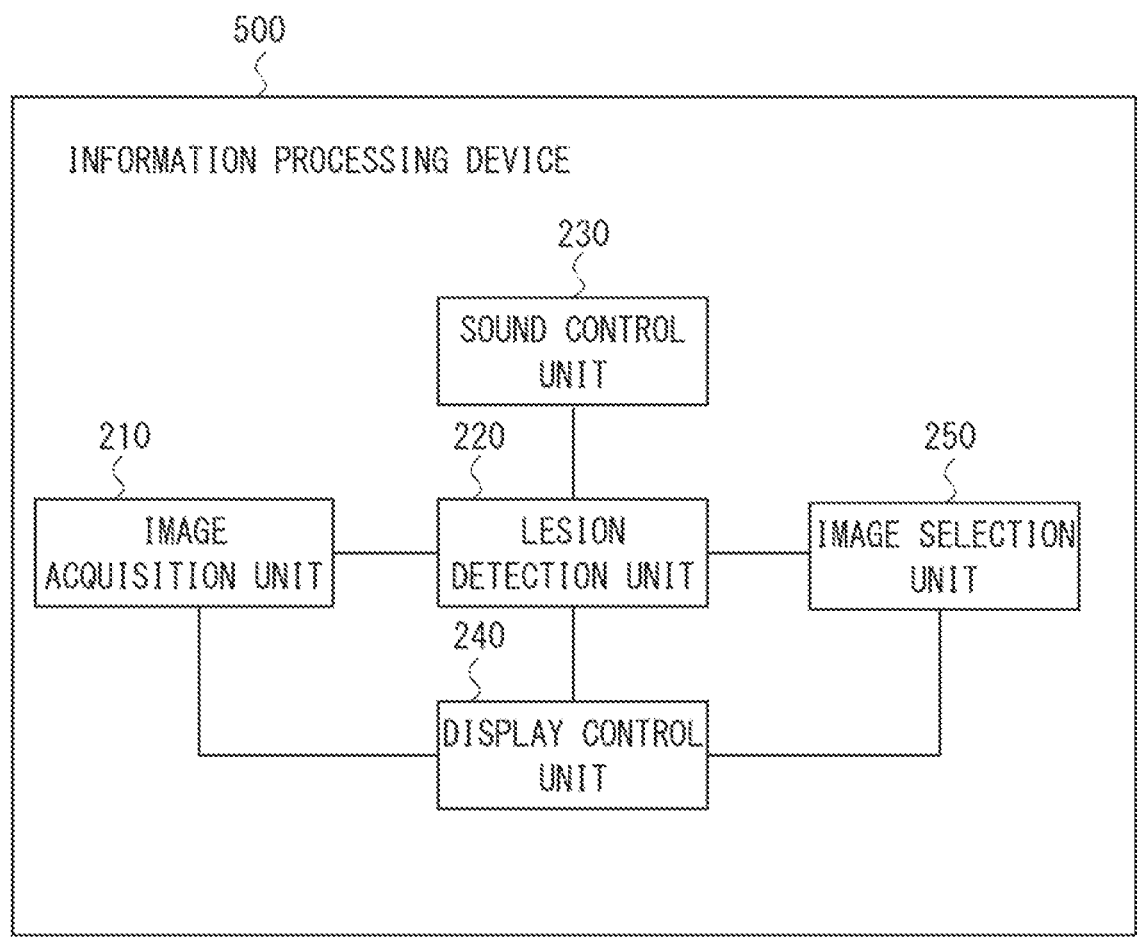
FIG. 9 is a block diagram showing an example of a functional configuration of an information processing device according to a fourth example embodiment.

FIG. 9 is a block diagram showing an example of a functional configuration of the information processing device 500 according to the fourth example embodiment. As shown in FIG. 9, the information processing device 500 differs from the information processing device 200 in that an image selection unit 250 is further provided. Processing of the image selection unit 250 is realized when a processor 292 reads and executes software (computer program) from a memory 291 for example.

The image selection unit 250 specifies a plurality of images in which the same lesion site is detected by the detection processing of the lesion detection unit 220, and selects one image (hereinafter, referred to as a representative image) from the plurality of specified images. In other words, the image selection unit 250 specifies a plurality of lesion images, in which the same lesion site is detected, and selects a representative image from the plurality of lesion images.

For example, the image selection unit 250 compares the lesion images with each other to specify a plurality of lesion images in which the same lesion site is detected. More specifically, the image selection unit 250 performs object track processing using feature points of the lesion site on continuous captured images (frame image) constituting the captured moving image, and thus specifies a plurality of lesion images in which the same lesion site is detected. By such processing, a plurality of images are specified in which the same lesion site is depicted, the plurality of images being obtained when the same lesion site is continuously captured in time. Then, the image selection unit 250 selects a representative image from the plurality of lesion images in which the same lesion site is detected. The image selection unit 250 selects, for example, a lesion image having the highest detection accuracy in the detection processing from these plurality of lesion images. When there are a plurality of lesion images having the highest detection accuracy in the detection processing, the image selection unit 250 may select, from these lesion images, an image in which the lesion site can be easily seen. For example, the image selection unit 250 may select an image in which position of the lesion site is closest to the center of the image, as the image in which the lesion site is easily seen, or may select an image in which the contrast between the lesion site and the non-lesion site is maximum.

The image selection unit 250 may specify a plurality of lesion images, in which the same lesion site is detected, by processing of calculating the similarity of images instead of the object track processing. In this case, it is possible to specify a plurality of images in which the same lesion site is depicted even when the same lesion site is not continuously captured in time.

Further, the display control unit 240 of the present example embodiment sets, as the display target of the degree of lapse of time, only the lesion image selected by the image selection unit 250 among the plurality of lesion images in which the same lesion site is detected. In other words, the display control unit 240 does not set, as the display target of the degree of lapse of time, the lesion image which is not selected by the image selection unit 250 from the plurality of lesion images in which the same lesion site is detected.

More specifically, in the present example embodiment, the display control unit 240 sets, as the display target of the degree of lapse of time, the lesion image for which the lapse of time is within the range of the time axis 65, the lesion image satisfying either (1) or (2) below:
  (1) lesion images that are not specified as a plurality of lesion images in which the same lesion site is detected by the image selection unit 250, that is, lesion images in which the detected lesion site does not overlap with other lesion images; and
  (2) lesion images that are selected as representative images by the image selection unit 250.

Similarly, the display control unit 240 of the present example embodiment sets, as the display target in the lesion image area 60, only the lesion image selected by the image selection unit 250 among the plurality of lesion images in which the same lesion site is detected. In other words, the display control unit 240 does not set, as the display target in the lesion image area 60, the lesion image which is not selected by the image selection unit 250 from the plurality of lesion images in which the same lesion site is detected.

More specifically, in the present example embodiment, the display control unit 240 sets, as the display target, a maximum of N (where N is a positive integer) lesion images detected most recently among the lesion images satisfying either (1) or (2) below:
  (1) lesion images that are not specified as a plurality of lesion images in which the same lesion site is detected by the image selection unit 250, that is, lesion images in which the detected lesion site does not overlap with other lesion images; and
  (2) lesion images that are selected as representative images by the image selection unit 250.

The fourth example embodiment has been described above. According to the present example embodiment, even when the lesion detection unit 220 detects the same lesion site in a plurality of images, the image selection unit 250 selects an image as a display target. For this reason, the visibility of the display is prevented from deteriorating.

Various modifications can be considered for each of the above-described example embodiments. For example, in the above-described example embodiments, the examination support system 10 includes the display device 140 and the display device 300, but the display device 140 may not be provided. In the above-described example embodiments, the display control unit 240 displays the image, in which the lesion site is detected, in the lesion image area 60, and displays the current image, which is captured by the endoscope 110, in the captured image area 63, but either of the images or both of the images may not be displayed.

Although the present invention is described above with reference to the example embodiments, the present invention is not limited to the above-described example embodiments. Various modifications that can be understood by those skilled in the art can be made to the configuration and details of the present invention within the scope of the present invention.

Some or all of the above-described example embodiments may also be described as in the following supplementary notes, but are not limited to the following.

(Supplementary Note 1)
  An information processing device comprising:
  an image acquisition unit configured to sequentially acquire a current image captured by an endoscope;
  a lesion detection unit configured to sequentially perform detection processing of a lesion site on the images sequentially acquired by the image acquisition unit; and
  a display control unit configured to display, on a display device, a degree of lapse of time up to a current time from a capturing time of the image in which the lesion site is detected by the lesion detection unit.

(Supplementary Note 2)
  The information processing device according to Supplementary note 1, wherein the display control unit displays a mark indicating the capturing time of the image, in which the lesion site is detected by the lesion detection unit, on a time axis with the current time as a starting point, and thus displays the degree of lapse.

(Supplementary Note 3)
  The information processing device according to Supplementary note 2, wherein the display control unit displays the mark depending on accuracy of detection in the detection processing.

(Supplementary Note 4)
  The information processing device according to Supplementary note 2 or 3, wherein when a plurality of lesion sites are detected on the same image by the lesion detection unit, the display control unit displays the mark depending on the number of detected lesion sites.

(Supplementary Note 5)
  The information processing device according to any one of Supplementary notes 1 to 4, wherein the display control unit displays the degree of lapse for an image, which is captured up to a time of a predetermined period ago from the current time, among the images sequentially acquired by the image acquisition unit.

(Supplementary Note 6)
  The information processing device according to any one of Supplementary notes 1 to 5, further comprising an image selection unit configured to specify a plurality of images in which the same lesion site is detected by the detection processing, and select a representative image from the plurality of specified images,
    wherein the display control unit sets, as a display target of the degree of lapse, only the image selected by the image selection unit among the plurality of images in which the same lesion site is detected.

(Supplementary Note 7)
  The information processing device according to any one of Supplementary notes 1 to 6, wherein the display control unit further displays the images in which the lesion site is detected by the lesion detection unit.

(Supplementary Note 8)
  The information processing device according to Supplementary note 7, wherein the display control unit further displays a position of the lesion site detected in the image by the lesion detection unit.

(Supplementary Note 9)
  The information processing device according to Supplementary note 7 or 8, wherein the display control unit further displays the current image sequentially acquired by the image acquisition unit and captured by the endoscope.

(Supplementary Note 10)
  The information processing device according to Supplementary note 1, wherein the display control unit is configured to:
    display a mark indicating the capturing time of the image, in which the lesion site is detected by the lesion detection unit, on a time axis with the current time as a starting point, and thus display the degree of lapse,
    display the image in which the lesion site is detected by the lesion detection unit, and
    display a line that associates a position of the lesion site detected in the image by the lesion detection unit with the mark.

(Supplementary Note 11)

The information processing device according to any one of Supplementary notes 1 to 10, further comprising a sound control unit configured to, when the lesion detection unit detects a lesion site, output a sound from a speaker to notify that the lesion site is detected.

(Supplementary Note 12)

A display method comprising:
sequentially acquiring a current image captured by an endoscope;
sequentially performing detection processing of a lesion site on the images sequentially acquired; and
displaying, on a display device, a degree of lapse of time up to a current time from a capturing time of the image in which the lesion site is detected.

(Supplementary Note 13)

A non-transitory computer-readable medium storing a program that causes a computer to execute:
an image acquisition step of sequentially acquiring a current image captured by an endoscope;
a lesion detection step of sequentially performing detection processing of a lesion site on the images sequentially acquired; and
a display control step of displaying, on a display device, a degree of lapse of time up to a current time from a capturing time of the image in which the lesion site is detected.

Reference Signs List

1 INFORMATION PROCESSING DEVICE
2 IMAGE ACQUISITION UNIT
3 LESION DETECTION UNIT
4 DISPLAY CONTROL UNIT
10 EXAMINATION SUPPORT SYSTEM
65 TIME AXIS
66 MARK
67 LINE
100 ENDOSCOPE SYSTEM
110 ENDOSCOPE
111 INSERTION PORTION
112 OPERATION PORTION
113 IMAGE CAPTURING PORTION
120 LIGHT SOURCE DEVICE
130 PROCESSOR DEVICE
140 DISPLAY DEVICE
200 INFORMATION PROCESSING DEVICE
210 IMAGE ACQUISITION UNIT
220 LESION DETECTION UNIT
230 SOUND CONTROL UNIT
240 DISPLAY CONTROL UNIT
250 IMAGE SELECTION UNIT
300 DISPLAY DEVICE
400 SPEAKER
500 INFORMATION PROCESSING DEVICE

The invention claimed is:

1. An information processing device comprising:
at least one memory storing program instructions; and
at least one processor configured to execute the instructions stored in the memory to:
sequentially acquire a current image captured by an endoscope;
sequentially perform detection processing of a lesion site on the images sequentially acquired; and
display, on a display device, a degree of lapse of time up to a current time from a capturing time of the image in which the lesion site is detected, wherein
the processor is configured to execute the instructions to:
display a mark indicating the capturing time of the image, in which the lesion site is detected, on a time axis with the current time as a starting point, thereby displaying the degree of lapse,
display a plurality of the images in which the lesion site is detected, and
display a plurality of lines, each of which associates a position of the detected lesion site in the image with the mark.

2. The information processing device according to claim 1, wherein the processor is configured to execute the instructions to display the mark depending on an accuracy of detection in the detection processing.

3. The information processing device according to claim 1, wherein the processor is configured to execute the instructions to, when a plurality of lesion sites are detected on the same image, display the mark depending on a number of detected lesion sites.

4. The information processing device according to claim 1, wherein the processor is configured to execute the instructions to display the degree of lapse for an image, which is captured up to a time of a predetermined period ago from the current time, among the images sequentially acquired.

5. The information processing device according to claim 1, wherein the processor is further configured to execute the instructions to:
specify a plurality of images in which the same lesion site is detected by the detection processing, and select a representative image from the plurality of specified images, and
set, as a display target of the degree of lapse, only the selected image among the plurality of images in which the same lesion site is detected.

6. The information processing device according to claim 1, wherein the processor is configured to execute the instructions to further display the position of the lesion site detected in the image.

7. The information processing device according to claim 1, wherein the processor is configured to execute the instructions to further display the current image sequentially acquired and captured by the endoscope.

8. The information processing device according to claim 1, wherein the processor is further configured to execute the instructions to, when a lesion site is detected, output a sound from a speaker to notify that the lesion site is detected.

9. A display method comprising:
sequentially acquiring a current image captured by an endoscope;
sequentially performing detection processing of a lesion site on the images sequentially acquired;
displaying a mark on a time axis with a current time as a starting point, thereby displaying a degree of lapse on a display device, the mark indicating a capturing time of the image in which the lesion site is detected, the degree of lapse being a degree of lapse of time up to the current time from the capturing time of the image in which the lesion site is detected;
displaying a plurality of the images in which the lesion site is detected; and
displaying a plurality of lines, each of which associates a position of the detected lesion site in the image with the mark.

10. A non-transitory computer-readable medium storing a program that causes a computer to execute:
sequentially acquiring a current image captured by an endoscope;

sequentially performing detection processing of a lesion site on the images sequentially acquired; and displaying, on a display device, a degree of lapse of time up to a current time from a capturing time of the image in which the lesion site is detected, wherein the displaying comprises:

displaying a mark indicating the capturing time of the image, in which the lesion site is detected, on a time axis with the current time as a starting point, thereby displaying the degree of lapse, displaying a plurality of the images in which the lesion site is detected, and displaying a plurality of lines, each of which associates a position of the detected lesion site in the image with the mark.

* * * * *